| United States Patent [19] | [11] Patent Number: 4,902,659 |
| Kelkar et al. | [45] Date of Patent: Feb. 20, 1990 |

[54] PREPARATION OF IMPROVED NICKEL-CONTAINING CATALYST AND PROCESS FOR CONVERSION OF ALCOHOLS TO CARBOXYLIC ACIDS THEREWITH

[75] Inventors: Ashutosh A. Kelkar; Rengaswamy Jaganathan; Devidas S. Kolhe; Raghunath V. Chaudhari, all of Pune, India

[73] Assignee: Council of Scientific and Industrial Research, New Delhi, India

[21] Appl. No.: 217,948

[22] Filed: Jul. 12, 1988

[51] Int. Cl.$^4$ .............................................. B01J 31/22
[52] U.S. Cl. .................... 502/167; 562/519; 260/413
[58] Field of Search ................. 502/167; 562/519; 260/413 J

[56] References Cited

U.S. PATENT DOCUMENTS

| 4,336,399 | 6/1982 | Isshiki et al. ................. 562/519 X |
| 4,659,518 | 4/1987 | Rizkalla .......................... 502/167 X |
| 4,661,631 | 4/1987 | Becker et al. .................. 562/519 X |

FOREIGN PATENT DOCUMENTS 90443 10/1983 European Pat. Off. ............ 562/519

*Primary Examiner*—Patrick P. Garvin
*Attorney, Agent, or Firm*—Ladas & Parry

[57] ABSTRACT

The present invention provides a process for the preparation of an improved nickel-containing catalyst suitable for the conversion of alcohols to the corresponding carboxylic acid which involves combining a nickel compound, an N-containing organic compound and an iodine promoter, bringing the combination in contact with an alcohol in the presence of carbon monoxide and subjecting the mixture to a temperature and pressure sufficient to initiate carbonylation of the alcohol. The process is characterized in that the N-containing organic compound is isoquinoline or a derivative thereof.

37 Claims, No Drawings

PREPARATION OF IMPROVED NICKEL-CONTAINING CATALYST AND PROCESS FOR CONVERSION OF ALCOHOLS TO CARBOXYLIC ACIDS THEREWITH

The present invention relates to an improved nickel-containing catalyst, its preparation and its employment for the catalytic conversion of alcohols to the corresponding carboxylic acids. The alcohols which can be so converted are essentially methanol but also include higher alcohols such as ethanol, propanol, n-butanol and higher homologues. In the description which follows, the invention will be described essentially in terms of the preparation of the improved catalyst and its employment for the conversion of methanol by the reaction with carbon monoxide to acetic acid. However, it must be understood that the invention is equally applicable to the conversion of other alcohols as well.

The prior art has proposed a number of catalysts for employment in processes for the preparation of carboxylic acids, particularly acetic acid. The best known of such catalysts are the homogeneous catalysts. Unfortunately, most of the catalysts proposed evince disadvantages during the course of their employment for the preparation of carboxylic acids. These disadvantages include the requirement of severe conditions of reaction, the loss of volatile catalysts and highly complex and expensive recycle/recovery systems.

The initial processes for the catalytic conversion of alcohols to carboxylic acids were those of Deutsche Offenlegungschrift Nos. 902495, 933148, 2303271 and 2400534. These processes proposed the use of cobalt complex catalysts but required very severe operating conditions including temperatures in the range of from 250° C. to 300° C. and pressures of from 680 to 700 atmospheres. These high temperatures and pressures were necessary in order to stabilise the active catalysts during the carbonylation of the alcohol, e.g. methanol to acetic acid. Furthermore, these former processes involved very complex separation techniques and the selectivity of the final acetic product was low.

According to French Pat. No. 1573130, South African Pat. No. 68/2174, U.S. Pat. No. 3689533 and U.S. Pat. No. 3769326, processes are described for the carbonylation of methanol employing as catalysts noble metals of Group VIII of the Periodic Table such as rhodium, iridium and platinum in the presence of bromine or iodine compounds as promotors. Other patents which describe the carbonylation of methanol specifically employing rhodium complex catalysts with iodine compound promotors include German Pat. Nos. 1941449 and 1939286, British Pat. No. 1233121, U.S. Pat. No. 3816490 and the above-mentioned South African Pat. No. 68/2174. Such process are also described in Chemical Tech., Oct. 1971, 600 to 605. These processes operate at lower pressures of carbon monoxide than the earlier processes employing cobalt catalyst complexes and yield a higher selectivity of the final acetic acid product, particularly, when rhodium is the catalyst employed. However, such processes suffer from the drawback that rhodium is a very expensive ingredient and the systems devised for its indispensible recovery are extremely complex thereby increasing the expense involved. For this reason, such processes are economical only when worked on a very large scale.

Later on, U.S. Pat. Nos. 4134912 and 4356320 have described processes for the preparation of acetic acid employing nickel catalysts along with triphenyl phosphine and tetraphenyl tin. These processes can be carried out at lower temperatures and pressures and to that extent are more economical than earlier processes. Unfortunately, the two U.S. patents in question report extremely poor selectivity for acetic acid when compared with the earlier processes employing rhodium catalysts.

Consequently, it is a principal object of the present invention to provide an improved catalyst for the carbonylation of alcohols to convert them to carboxylic acids which avoids the disadvantages inherent in prior art catalysts employed for the same purpose.

A more specific object resides in the provision of an improved catalyst for the above-mentioned purpose which avoids employing expensive noble metals therefor, can be employed under moderate operating conditions and which evinces high activity and high selectivity for the preparation of the carboxylic acids.

Yet another object of the invention resides in a process which employs the above-stated improved catalyst for the conversion by carbonylation of alcohols to carboxylic acids.

As a result of their research, the applicants have been able to ascertain that the activity of a nickel catalyst can be significantly enhanced when the nickel compound is in combination with a N-containing organic compound and a promotor. In addition, the employment of a co-catalyst still further enhances the catalytic activity of the catalyst composite with respect to the carbonylation of alcohol to convert it to carboxylic acid.

Accordingly, the present invention provides a process for the preparation of an improved nickel-containing catalyst suitable for the conversion of alcohols to the corresponding carboxylic acids which comprises combining a nickel compound, a N-containing organic compound and an iodine promotor, bringing the combination so formed into contact with an alcohol in the presence of carbon monoxide and subjecting the mixture to elevated temperature and pressure so as to initiate carbonylation of the alcohol with the instantaneous production in situ of said catalyst as an interactive composite of the nickel compound, N-containing organic compound and iodine promotor.

The invention also provides a process for the conversion of alcohols to the corresponding caboxylic acids which comprises combining a nickel compound, a N-containing organic compound and an iodine promotor, bringing the combination so formed into contact with an alcohol in the presence of carbon monoxide and subjecting the mixture to elevated temperature and pressure so as to initiate carbonylation of the alcohol with the instantaneous production in situ of a catalyst comprising an interactive composite of nickel compound, N-containing organic compound and iodine promotor and maintaining the reaction until carbonylation of the alcohol and conversion to the carboxylic acid was complete.

The preparation of the improved catalyst and the conversion therewith of alcohols to carboxylic acids is preferably effected in the presence of a solvent. This solvent can be any monocarboxylic acid such as acetic acid or propionic acid. The temperature for the reaction can be in the range of from 100° C. to 300° C. and a particularly preferable range is from 150° C. to 250° C.

The preparation of the catalyst and the conversion of alcohols to carboxylic acids can be effected at a partial pressure of carbon monoxide of from 5 psig to 3000 psig, preferably 200 psig to 1000 psig. It is particularly preferred to employ a two-stage pressurisation of the reaction mixture. Thus, the mixture can be pressurised with carbon monoxide to 200 psig until the maximum temperature for the reaction has been attained whereupon pressure is increased to about 1000 psig. As a variation of this, even a three-stage pressurisation can be followed with the mixture being first pressurised with carbon monoxide to 50 psig, then with hydrogen to 200 psig and finally with carbon monoxide again to 1000 psig.

The catalyst resulting from the process of the present invention is capable of tolerating the presence in the carbon monoxide gas employed for the pressurisation of impurities such as hydrogen, nitrogen and carbon dioxide without adversely affecting the carbonylation reaction. In fact, the presence of hydrogen has been found to be beneficial towards achieving high activity and selectivity of the prepared catalysts. In this connection, it has been established that the ratio of hydrogen to carbon monoxide in the pressurising gas can be from 1 to 20, preferably from 1 to 10.

In accordance with a preferred feature, the process of the invention for preparation of the improved catalyst for conversion of alcohols to carboxylic acids employs 1 mole of the nickel compound for every 5 to 8000 moles of the alcohol. A preferred ratio is 1 mole of nickel compound for every 20 to 100 moles of alcohol.

According to a further feature, the process preferably employs 1 mole of the N-containing organic compound for every 20 to 5000 moles of alcohol, preferably 1 mole of the N-containing organic compound for every 40 to 100 moles of alcohol.

According to a preferred embodiment, an alkali metal halide co-catalyst for the reaction is incorporated into the reaction mixture. The alkali metal halide employed may be selected from potassium chloride, potassium iodide, sodium iodide, lithium iodide and lithium chloride.

The nickel compound employed in the process of the invention can be any of a variety of nickel salts leading to comprable activity and selectivity. These nickel compounds can be selected from nickel chloride, nickel iodide, nickel bromide, nickel acetate and nickel powder.

The N-containing organic compound which can be employed is selected from isoquinoline, pyridine, 3-picoline and the like.

The iodine promotor can be an iodine compound such as methyl iodide, ethyl iodide, hydroiodic acid and the like.

The process of the invention can be employed for the carbonylation of alcohols to convert them to the corresponding carboxylic acids. It is particularly suitable for the carbonylation of methanol or propanol for conversion to acetic acid and/or methyl acetate and propionic acid, respectively. The reaction can conveniently be carried out in a stirred pressure reactor with the improved catalyst employed in a homogeneous phase with a suitable solvent.

After the reaction is complete, the volatile promotor and the carboxylic acid end product are separated from the catalyst composite in any known manner, such as distillation. The catalyst and the promotor are recycled for additional use while the crude carboxylic acid produced is processed further in order to purify it.

The improved catalyst prepared by the process of the present invention when employed for the conversion of alcohols to carboxylic acids evinces selectivity to the acids at least equal to that of the prior art rhodium catalysts. The great advantage, of course, of the catalyst of this invention is that it is several times cheaper to produce than the earlier rhodium catalysts. It is believed that it is the combined effect of the nickel compound, N-containing organic compound and iodine promotor which causes the catalyst of this invention to evince this selectivity when employed for the conversion of alcohols to carboxylic acids.

The invention will now be described in greater detail in the following non-limitative examples each of which is representative of the combined preparation of the improved catalyst of the invention and its employment for the manufacture of the preferred carboxylic acids e.g. acetic acid and propionic acid.

EXAMPLE 1

A 300 ml stirred autoclave was charged with the following reactants:
Methanol: 0.4937 mols
Methyl iodide: 0.08 mols
$NiCl_2 \cdot 6H_2O$: 0.0084 mols
Isoquinoline: 0.0168 mols
Acetic acid (solvent): 1.3112 mols The contents of the autoclave were flushed with nitrogen and then with carbon monoxide. Thereafter, the autoclave was pressurised with carbon monoxide to 200 psig and the contents heated to 225° C. After this temperature was attained, the autoclave was pressurised to 1000 psig with carbon monoxide. It was observed that immediately after the desired temperature was reached, carbon monoxide absorption commenced immediately. This confirmed that the active catalyst for the carbonylation reaction was formed in situ instantaneously when the methanol, iodine promotor, i.e. methyl iodide, nickel chloride and isoquinoline were contacted together under reaction conditions in the presence of carbon monoxide in the gaseous phase.

For preparation of the final acetic acid product, the pressure in the autoclave was maintained constant at 1000 psig and the progress of the reaction was monitored by observing the pressure drop in the carbon monoxide reservoir. The reaction was continued until the pressure drop stopped completely. The reactor was then cooled and the liquid phase analysed by gas chromatography (GC).

After 3.5 hours, the GC analysis showed 97% conversion of methanol with 98.46% selectivity to acetic acid.

EXAMPLE 2

A catalyst was prepared in accordance with the procedure of Example 1 except that nickel iodide was used instead of nickel chloride. In this instance also, carbon monoxide absorption commenced immediately after the desired temperature was attained indicating instantaneous formation of the active catalytic species. Thereafter, preparation of the final acetic acid product was carried out as in Example 1.

After 3.0 hours, the GC analysis showed 99% conversion of methanol with 96.8% selectivity to acetic acid.

EXAMPLE 3

A catalyst was prepared in accordance with the procedure of Example 1 with the exception that nickel bromide was used instead of nickel chloride. Here too, carbon monoxide absorption commenced immediately after the desired temperature was attained indicating instantaneous formation of the active catalytic species. Thereafter, preparation of the final acetic acid product was carried out as in Example 1.

After 4.0 hours, the GC analysis showed 98.7% conversion of methanol with 97% selectivity to acetic acid.

EXAMPLE 4

A catalyst was prepared in accordance with the procedure of Example 1 except that nickel acetate was used instead of nickel chloride. In this case also, carbon monoxide absorption commenced immediately after the desired temperature was attained indicating instantaneous formation of the active catalytic species. Thereafter, preparation of the final acetic acid product was carried out as in Example 1.

After 3.7 hours, the GC analysis showed 98.5% conversion of methanol with 97.8% selectivity to acetic acid.

EXAMPLE 5

A catalyst was prepared according to the procedure of Example 1 except that iodine was used as a promotor instead of methyl iodide. As in the earlier examples, carbon monoxide absorption commenced immediately after the desired temperature was attained indicating instantaneous formation of the active catalytic species. Thereafter, preparation of the final acetic acid product was carried out as in Example 1.

After 3.7 hours, the GC analysis showed 98.5% conversion of methanol with 97.8% selectivity to acetic acid.

EXAMPLE 6

A catalyst was prepared according to the procedure of Example 1 except that aqueous hydroiodic acid was used as a promotor instead of methyl iodide. Here again, carbon monoxide absorption commenced immediately after the desired temperature was attained indicating instantaneous formation of the active catalytic species. Thereafter, preparation of the final acetic acid product was carried out as in Example 1.

After 3.6 hours, the GC analysis showed 97.5% conversion of methanol with 99% selectivity to acetic acid.

EXAMPLE 7

A catalyst was prepared according to the procedure of Example 1 except that 0.0168 mols pyridine was used instead of isoquinoline. Here again, carbon monoxide absorption commenced immediately after the desired temperature was attained indicating instantaneous formation of the active catalytic species. Thereafter, preparation of the final acetic acid product was carried out as in Example 1.

After 4.5 hours, the GC analysis showed 99.8% conversion of methanol with 95.5% selectivity to acetic acid.

EXAMPLE 8

A catalyst was prepared according to the procedure of Example 1 except that 0.0168 mols 3-picoline was used instead of isoquinoline. Here again, carbon monoxide absorption commenced immediately after the desired temperature was attained indicating instantaneous formation of the active catalytic species. Thereafter, preparation of the final acetic acid product was carried out as in Example 1.

After 4.5 hours, the GC analysis showed 99.8% conversion of methanol with 92% selectivity to acetic acid.

EXAMPLE 9

A 300 ml stirred autoclave was charged with the following reactants:
Methanol: 0.4937 mols
Methyl iodide: 0.08 mols
$NiCl_2 \cdot 6H_2O$: 0.0084 mols
Isoquinoline: 0.0168 mols
Potassium chloride: 0.0168 mols
Acetic acid (solvent): 1.3112 mols The contents of the autoclave were flushed with nitrogen and then with carbon monoxide. Thereafter, the autoclave was pressurised with carbon monoxide to 200 psig and the contents heated to 225° C. After this temperature was attained, the autoclave was pressurised to 1000 psig with carbon monoxide. It was observed that immediately after the desired temperature was reached, carbon monoxide absorption commenced immediately. This confirmed that the active catalyst for the carbonylation reaction was formed in situ instantaneously when the methanol, iodine promoter, i.e. methyl iodide, nickel chloride, isoquinoline and potassium chloride were contacted together under reaction conditions in the presence of carbon monoxide in the gaseous phase.

For preparation of the final acetic acid product, the pressure in the autoclave was maintained constant at 1000 psig and the progress of the reaction was monitored by observing the pressure drop in the carbon monoxide reservoir. The reaction was continued until the pressure drop stopped completely. The reactor was then cooled and the liquid phase analysed by gas chromatography (GC).

After 4.0 hours, the GC analysis showed 94.6% conversion of methanol with 95.3% selectivity to acetic acid.

EXAMPLE 10

A catalyst was prepared according to the procedure of Example 9 except that lithium chloride was used as co-catalyst instead of potassium chloride. Here again, carbon monoxide absorption commenced immediately after the desired temperature was attained indicating instantaneous formation of the active catalytic species. Thereafter, preparation of the final acetic acid product was carried out as in Example 9.

After 3.5 hours, the GC analysis showed 98.5% conversion of methanol with 94% selectivity to acetic acid.

EXAMPLE 11

A catalyst was prepared according to the procedure of Example 9 except that potassium iodide was used as co-catalyst instead of potassium chloride. Here again, carbon monoxide absorption commenced immediately after the desired temperature was attained indicating instantaneous formation of the active catalytic species. Thereafter, preparation of the final acetic acid product was carried out as in Example 9.

After 2.2 hours, the GC analysis showed 97.6% conversion of methanol with 86.7% selectivity to acetic acid.

EXAMPLE 12

A catalyst was prepared according to the procedure of Example 9 except that sodium iodide was used as co-catalyst instead of potassium chloride. Here again, carbon monoxide absorption commenced immediately after the desired temperature was attained indicating instantaneous formation of the active catalytic species. Thereafter, preparation of the final acetic acid product was carried out as in Example 9.

After 2.6 hours, the GC analysis showed 95.3% conversion of methanol with 99% selectivity to acetic acid.

EXAMPLE 13

A catalyst was prepared according to the procedure of Example 9 except that lithium iodide was used as co-catalyst instead of potassium chloride. Here again, carbon monoxide absorption commenced immediately after the desired temperature was attained indicating instantaneous formation of the active catalytic species. Thereafter, preparation of the final acetic acid product was carried out as in Example 9.

After 2.0 hours, the GC analysis showed 99.7% conversion of methanol with 98% selectivity to acetic acid.

EXAMPLE 14

A catalyst was prepared according to the procedure of Example 13 except that nickel iodide was used as catalyst instead of nickel chloride. Once again, carbon monoxide absorption commenced immediately after the desired temperature was attained indicating instantaneous formation of the active catalytic species. Thereafter, preparation of the final acetic acid product was carried out as in Example 13.

After 1.9 hours, the GC analysis showed 99.0% conversion of methanol with 98.5% selectivity to acetic acid.

EXAMPLE 15

A catalyst was prepared according to the procedure of Example 13 except that hydrogen was introduced into the reactor initially such that the ratio of carbon monoxide to hydrogen in the autoclave was 5:1. As usual, carbon monoxide absorption commenced immediately after the desired temperature was attained indicating instantaneous formation of the active catalytic species. Thereafter, preparation of the final acetic acid product was carried out as in Example 13.

After 1.2 hours, the GC analysis showed 100% conversion of methanol with 97.4% selectivity to acetic acid.

EXAMPLE 16

A catalyst was prepared in accordance with the procedure of Example 1 except that the temperature for the reaction was 235° C. As usual, carbon monoxide absorption commenced immediately after the desired temperature was attained indicating instantaneous formation of the active catalytic species. Thereafter, preparation of the final acetic acid product was carried out as in Example 1.

After 3.0 hours, the GC analysis showed 98% conversion of methanol with 99% selectivity to acetic acid.

EXAMPLE 17

A 300 ml stirred autoclave was charged with the following reactants:
Ethanol: 0.3472 mols
Ethyl iodide: 0.062 mols
$NiCl_2 \cdot 6H_2O$: 0.0084 mols
Isoquinoline: 0.0168 mols
Lithium iodide: 0.0168 mols
Propionic acid (solvent): 1.0023 mols The contents of the autoclave were flushed with nitrogen and then with carbon monoxide. Thereafter, the autoclave was pressurised with carbon monoxide to 50 psig and then with hydrogen up to 200 psig and the contents heated to 225° C. After this temperature was attained, the autoclave was pressurised to 1000 psig with carbon monoxide. It was observed that immediately after the desired temperature was reached, carbon monoxide absorption commenced immediately. This confirmed that the active catalyst for the carbonylation reaction was formed in situ instantaneously when the ethanol, iodine promotor, i.e. ethyl iodide, nickel chloride, isoquinoline and lithium iodide were contacted together under reaction conditions in the presence of carbon monoxide in the gaseous phase.

For preparation of the final acetic acid product, the pressure in the autoclave was maintained constant at 1000 psig and the progress of the reaction was monitored by observing the pressure drop in the carbon monoxide reservoir. The reaction was continued until the pressure drop stopped completely. The reactor was then cooled and the liquid phase analysed by gas chromatography (GC).

After 3.0 hours, the GC analysis showed 98.5% conversion of ethanol with 97.8% selectivity to propionic acid.

From the Examples contained above, the following observations can be gleaned. Referring to Examples 1, 7 and 8, it is seen that best results are obtained when isoquinoline is employed as the N-containing organic compound. Where a co-catalyst is employed (Examples 9 to 14) it is lithium iodide (Example 13) which provides best results in terms of improved activity and selectivity. From Example 15, it is clear that dilution of the feed carbon monoxide with hydrogen has no adverse effect on the carbonylation reaction. In fact, the presence of hydrogen actually enhances the activity of the catalyst without affecting a selectivity. Finally, Example 17 proves that the catalyst of the invention can also be employed for the conversion of higher alcohols to acids.

It only remains to compare the results of the process of this invention with the processes of prior U.S. Pat. Nos. 4134912 and 4356320 in which the use of nickel catalysts for the preparation of acetic acid has been proposed. Such a comparison reveals that the end products of the U.S. patents contain in addition to the desired acetic acid other components such as methyl acetate and dimethyl ether. Thus, under those patents, the selectivity for acetic acid was in the range of 60% to 90%. The present invention, on the other hand, reflects a 95% to 100% conversion of methanol to acetic acid with a 98% selectivity for the acid. This is considered a significant improvement over the U.S. prior art.

What the applicants claim as their invention is now set out in the claims which follow hereafter.

We claim:
1. In a process for the preparation of an improved nickel-containing catalyst suitable for the conversion of alcohols to the corresponding carboxylic acids which involves combining a nickel compound, an N-containing organic compound and an iodine promoter, bringing the combination into contact with an alcohol in the presence of carbon monoxide and subjecting the mixture to a temperature and pressure sufficient to initiate carbonylation of the alcohol and the instantaneous production in situ of said catalyst as an interactive composite of the nickel compound, N-containing organic com- pound and iodine promoter, the improvement comprising employing isoquinoline as the N-containing organic compound.

2. A process as claimed in claim 1, wherein the reaction is effected in the presence of a monocarboxylic acid solvent.

3. A process according to claim 2, wherein said monocarboxylic acid is acetic or propionic acid.

4. A process as claimed in claim 1, wherein said reaction is effected at a temperature in the range from 100° C. to 300° C.

5. A process as claimed in claim 4, wherein said reaction is effected at a temperature in the range from 150° C. to 250° C.

6. A process as claimed in claim 1, wherein said carbon monoxide gas employed for pressurization contains hydrogen, the ratio of hydrogen to carbon monoxide in the gas being from 1 to 20.

7. A process according to claim 6, wherein the ratio of hydrogen to carbon monoxide is 1 to 10.

8. A process as claimed in claim 1, wherein said reaction is effected under a pressure of from 6 psig to 3000 psig.

9. A process according to claim 8, wherein said reaction is effected under a pressure of 200 psig to 1000 psig.

10. A process according to claim 9, wherein said pressure is applied in two stages, first to about 200 psig and, after the desired temperature for the reaction has been obtained, is increased to about 1000 psig.

11. A process as claimed in claim 10, wherein said pressure is applied in three stages, first with carbon monoxide to about 50 psig followed by hydrogen to about 200 psig and finally with carbon monoxide again to about 1000 psig.

12. A process as claimed in claim 1, wherein the reaction mixture includes 1 mole of the nickel compound for every 5 to 8000 moles of the alcohol.

13. A process according to claim 12, wherein the reaction mixture includes 1 mole of nickel compound for every 20 to 100 moles of alcohol.

14. A process as claimed in claim 1, wherein the reaction mixture includes 1 mole of the N-containing organic compound for every 20 to 5000 moles of alcohol.

15. A process according to claim 14, wherein the reaction mixture includes 1 mole of N-containing organic compound for every 40 to 100 moles of alcohol.

16. A process as claimed in claim 1, wherein an alkali metal halide co-catalyst selected from the group consisting of potassium chloride, potassium iodide, sodium iodide, lithium iodide and lithium chloride is incorporated into the reaction mixture.

17. A process as claimed in claim 1, wherein said nickel compound is selected from the group consisting of nickel chloride, nickel iodide, nickel bromide, nickel acetate and nickel powder.

18. A process as claimed in claim 1, wherein said iodine promotor is selected from the group consisting of methyl iodide, ethyl iodide and hydroiodic acid.

19. In a process for the conversion of alcohol to the corresponding carboxylic acid which involves combining a nickel compound, an N-containing organic compound and an iodine promoter, bringing the combination into contact with an alcohol in the presence of carbon monoxide and subjecting the mixture to a temperature and pressure sufficient to initiate carbonylation of the alcohol and the instantaneous production in situ of said catalyst as an interactive composite of the nickel compound, N-containing organic compound and iodine promoter, the improvement comprising employing isoquinoline or a derivative as the N-containing organic compound.

20. A process as claimed in claim 19, wherein the reaction is effected in the presence of a monocarboxylic acid solvent.

21. A process as claimed in claim 19, wherein said reaction is effected at a temperature in the range of from 100° C. to 300° C.

22. A process as in claim 21, wherein said reaction is effected at a temperature in the range of from 150° C. to 250° C.

23. A process as claimed in claim 19, wherein said carbon monoxide gas employed for pressurization contains hydrogen, the ratio of hydrogen to carbon monoxide in the gas being from 1 to 20.

24. A process according to claim 23, wherein the ratio of hydrogen to carbon monoxide is from 1 to 10.

25. A process as claimed in claim 19, wherein said reaction is effected under a pressure from 5 psig to 3000 psig.

26. A process according to claim 25, wherein said reaction is effected under a pressure of 200 psig to 1000 psig.

27. A process according to claim 26, wherein said pressure is applied in two stages, first to about 200 psig and, after the desired temperature for the reaction has been obtained, is increased to about 1000 psig.

28. A process as claimed in claim 27 wherein said pressure is applied in three stages, first with carbon monoxide to about 50 psig followed by hydrogen to about 200 psig and finally with carbon monoxide again to about 1000 psig.

29. A process as claimed in claim 19, wherein the reaction mixture includes 1 mole of the nickel compound for every 5 to 8000 moles of the alcohol.

30. A process according to claim 29, wherein the reaction mixture includes 1 mole of nickel compound for every 20 to 100 moles of the alcohol.

31. A process as claimed in claim 19, wherein the reaction mixture includes 1 mole of the N-containing organic compound for every 20 to 5000 moles of alcohol.

32. A process according to claim 31, wherein the reaction mixture includes 1 mole of N-containing organic compound for every 40 to 100 moles of alcohol.

33. A process as claimed in claim 19, wherein an alkali metal halide co-catalyst selected from the group consisting of potassium chloride, potassium iodide, sodium iodide, lithium iodide and lithium chloride is incorporated into the reaction mixture.

34. A process as claimed in claim 19, wherein said nickel compound is selected from the group consisting of nickel chloride, nickel iodide, nickel bromide, nickel acetate and nickel powder.

35. A process as claimed in claim 19, wherein said iodine promotor is selected from the group consisting of methyl iodide, ethyl iodide, and hydroiodic acid.

36. A process as claimed in claim 19, wherein said alcohol is selected from the group consisting of methanol, ethanol, propanol, n-butanol and other higher homologues.

37. A process as claimed in claim 19, wherein after the reaction is complete, the promotor and catalyst are separated from the carboxylic acid end product and are recycled for further use while the carboxylic acid is refined in order to purify.

* * * * *